United States Patent [19]

Chiu et al.

[11] Patent Number: 4,963,667
[45] Date of Patent: Oct. 16, 1990

[54] IVERMECTIN DERIVATIVE COMPOUNDS AND PROCESS FOR PREPARING THE SAME

[75] Inventors: Shuet-Hing L. Chiu, Westfield; Josephine R. Carlin, North Brunswick; Rae Taub, Metuchen, all of N.J.

[73] Assignee: Merck & Co., Inc., Rahway, N.J.

[21] Appl. No.: 452,641

[22] Filed: Dec. 19, 1989

Related U.S. Application Data

[63] Continuation-in-part of Ser. No. 119,454, Nov. 10, 1987, abandoned.

[51] Int. Cl.$^5$ .................................. C07H 17/08
[52] U.S. Cl. ........................................ 536/7.1
[58] Field of Search ........................ 514/30; 536/7.1

[56] References Cited

U.S. PATENT DOCUMENTS

| | | | |
|---|---|---|---|
| 4,199,569 | 4/1980 | Chabala et al. | 514/30 |
| 4,283,494 | 8/1981 | Kokusho et al. | 435/198 |
| 4,310,519 | 1/1982 | Albers-Schonberg et al. | 514/30 |
| 4,333,925 | 6/1982 | Buhs et al. | 514/30 |

OTHER PUBLICATIONS

Swell et al., "Cholesterol Esterases II, Characterization of the Esterifying Cholesterol Esterase of Pancreatin", *J. Biol. Chem.*, 182, 479–487, (1950).

Swell et al., "Enzymic Preparation of Labeled Unsaturated Fatty Acid Esters of Cholesterol", *Analytical Biochemistry*, 4, 335–340, (1962).

*Primary Examiner*—John W. Rollins
*Assistant Examiner*—W. Catchpole
*Attorney, Agent, or Firm*—Salvatore C. Mitri; Joseph F. DiPrima

[57] ABSTRACT

There are disclosed novel ivermectin compounds and a process for preparing them, the novel ivermectin compounds containing straight chain or branched fatty acid residues of from about $C_2$ to about $C_{20}$ and having the formula:

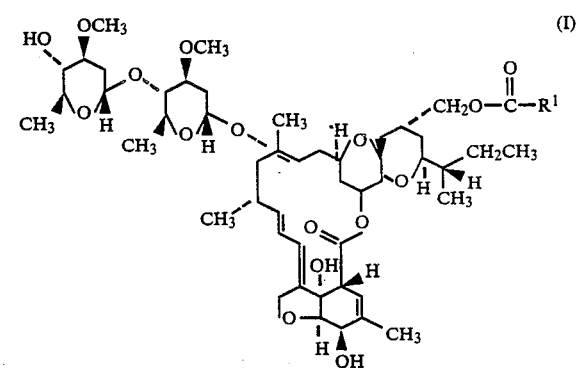

3 Claims, No Drawings

IVERMECTIN DERIVATIVE COMPOUNDS AND PROCESS FOR PREPARING THE SAME

INTRODUCTION OF THE INVENTION

This application is a continuation-in-part of copending application Ser. No. 119,454 filed Nov. 10, 1987 now abandoned.

This invention relates to novel ivermectin derivative compounds which are useful as antiparasitic agents. The compounds of this invention can be characterized as macrocyclic alcohols (i.e., cyclic compounds having rings containing seven or more carbon atoms) having straight chain or branched fatty acids of from about $C_2$ to about $C_{20}$.

The novel ivermectin derivative compounds of the invention have the formula:

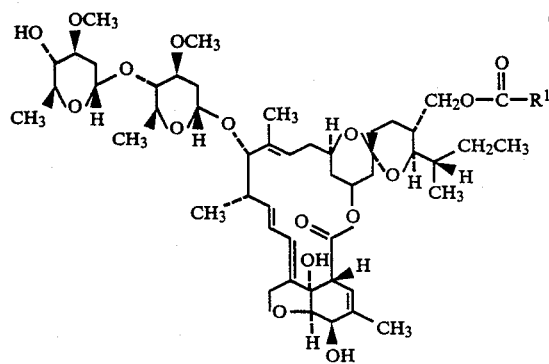

wherein $R^1$ is a straight chain or branched fatty acid of $C_2$–$C_{20}$.

BACKGROUND OF THE INVENTION

Enzymes such as, for example, cholesterol esterase, are known to be dual function enzymes capable of either synthesizing or hydrolyzing ester linkages. Under incubation conditions at an acidic pH, cholesterol esterase has been used to synthesize cholesterol esters of such fatty acids as palmitoleic oleic, and linoleic acids [L. Swell, et al., "Enzymatic Preparation of Labeled Unsaturated Fatty Acid Esters of Cholesterol", *Analy. Biochem*, 4, 335–340 (1962); L. Swell, et al., "Cholesterol Esterase II: Characterization of Pancreatin", *J. Biol. Chem.*, 182, 479–487 (1950)].

Ivermectin compounds, processes for their preparation and their utility are disclosed and described in U.S. Pat. Nos. 4,335,925; 4,310,519; and, 4,199,569 which are incorporated herein and made a part hereof by reference thereto. These ivermectin compounds are hereinafter collectively referred to as "parent ivermectin compounds." Thus, the compounds of this invention are fatty acid derivatives of these parent invermectin compounds.

SUMMARY OF THE INVENTION

Fatty acid esters of macrocyclic alcohols can be enzymatically synthesized in vitro using an esterase at an acidic pH enabling one to obtain a single, stereoselected product that is free from impurities and side products. Such a process is applicable to macrocyclic alcohols (i.e., cyclic compounds having rings containing seven or more C atoms) and to acids ranging from simple organic acids to straight chain or branched fatty acids of from about $C_2$ to about $C_{20}$.

Therefore, the process that can be used to obtain the compounds of the invention generally comprises incubating a macrocyclic alcohol with a fatty acid at ambient temperature in the presence of a bile salt and an enzyme at an acidic pH; extracting the resultant incubate to obtain an organic phase and an aqueous phase; and, evaporating the organic phase to obtain the desired fatty acid ester of the macrocyclic alcohol.

The macrocyclic alcohols that can be used in this process are the parent avermectin compounds disclosed and described in the U.S. Pat. Nos. identified above.

The fatty acids that can be employed in this process can range from simple organic acids to straight chain or branched fatty acids of from about $C_2$ to about $C_{20}$. Illustrative of such fatty acids are butyric, caproic, octanic, lauric, oleic, myristic, palmitic, stearic and arachidonic acids as well as fatty acids having more complex structures.

Conventional, commercially available bile salts can be readily used in the process such as sodium taurocholate, sodium cholate, deoxycholate, and the like. Of these, sodium taurocholate is preferred since it is economical and readily available.

Similarly, conventional, commercially available enzymes can be employed such as esterase, lipase, and the like and, because it is also economical and readily available, cholesterol esterase is preferred.

The pH of the aqueous incubation medium is adjusted to be slightly acidic such as from about pH 6.0 to about pH 6.5, preferably about pH 6.2 by using conventional mineral acids. If the pH is below about 6.0, it has been found to be difficult to obtain a desired product. When the pH is above about 7.0, it has been found that a desired product can be obtained, but at low yield.

Extraction of the resultant incubate can be typically accomplished by dissolving the incubate in a commonly used organic solvent such as chloroform, methylene chloride, ethyl acetate, and the like.

Where either the macrocyclic alcohol and/or the fatty acid employed is unsaturated or unstable, the evaporation step is preferably conducted under an inert atmosphere by using an appropriate inert gas such as nitrogen, argon, carbon dioxide, and the like.

Completion of the incubation step will vary depending upon both the macrocyclic alcohol and fatty acid employed, but can be readily monitored and determined by thin layer chromatography (TLC), high pressure liquid chromatography (HPLC), or other typically used chromatographic methods.

This process is further illustrated by the following general reaction scheme wherein R represents a fatty acid chain of $C_2$ to $C_{20}$ and $R^1$ represents the structure of a macrocyclic alcohol:

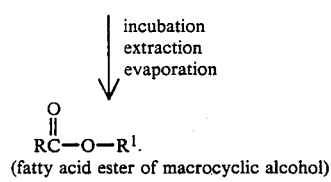

(fatty acid ester of macrocyclic alcohol)

DETAILED DESCRIPTION OF THE INVENTION

The novel ivermectin derivative compounds of the invention have the formula:

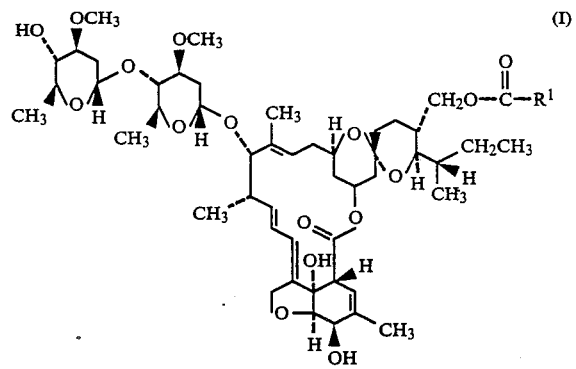

wherein $R^1$ is a straight chain or branched $C_2$–$C_{20}$ fatty acid; preferably $C_8$–$C_{20}$ such as $C_{13}H_{27}$; $C_{15}H_{31}$; $C_{17}H_{33}$; $CH_3(CH_2)_4(CH=CHCH_2)_4CH_2CH_2$; and the like.

It has been confirmed that macrocyclic alcohols; i.e., parent ivermectin compounds, are metabolized to their corresponding esters which have been found as mixtures of various fatty acids in the fatty tissue of host animals [S. L. Chiu, et al, *Drug Metabolism and Disposition*, 16, No. 5, 728–736 (1988); S. L. Chiu, et al, "Metabolism and Tissue Residues", *Ivermectin and Avermectin*, published by Springer Verlag (1989)]. The fatty acid derivative compounds of this invention were found to be a part of this fatty acid mixture found in the fatty tissue of host animals indicating that a host animal may not have to metabolize the compounds of this invention so that the invention compounds could be directly efficacious upon administration to a host animal.

Thus, the compounds of the invention are useful as anthelmintics, insecticides and acaricides in human and animal health and may have similar parasiticidal activity in agriculture. The disease or group of diseases for which the compounds of this invention can be used as an antiparasitic agent are disclosed and particularly described in the above identified U.S. Pat. No. 4,333,925.

The process which can be used to make the compounds of the invention is exemplified in the examples which follow wherein the ivermectin metabolic derivatives that were used in the process as the substrates are those disclosed and described in U.S. Pat. No. 4,333,925 identified hereinabove. These avermectin and ivermectin derivative compounds can be represented by the following structural formula:

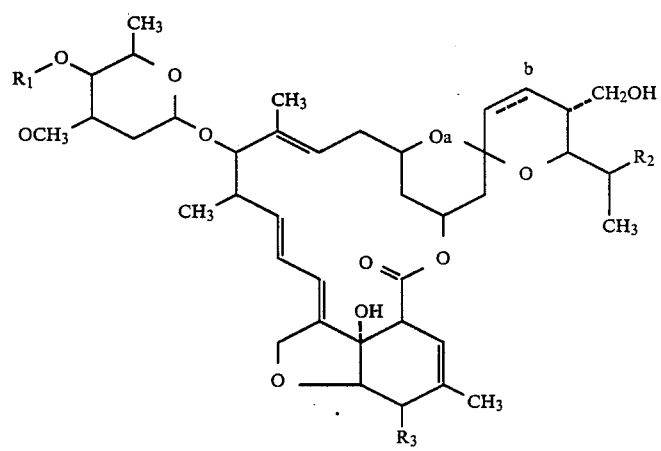

wherein $R^1$ is H or A wherein A is

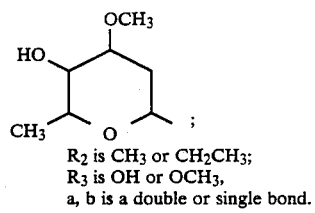

$R_2$ is $CH_3$ or $CH_2CH_3$;
$R_3$ is OH or $OCH_3$,
a, b is a double or single bond.

When a, b is a double bond, the series of compounds are avermectins and when a, b is a single bond, the series of compounds are ivermectins.

Ivermectin derivative compounds represented by the foregoing structure are shown in the following table wherein a, b is a single bond:

TABLE I

| | Metabolic Derivative Compounds | $R_1$ | $R_2$ | $R_3$ |
|---|---|---|---|---|
| I. | $H_2B_{1a}$ | A | $CH_2CH_3$ | OH |
| II. | $H_2B_{1b}$ | A | $CH_3$ | OH |
| III. | $H_2B_{1a}$-Monosaccharide ($H_2B_{1a}$-Ms) | H | $CH_2CH_3$ | OH |
| IV. | $H_2B_{1b}$-Monosaccharide ($H_2B_{1b}$-Ms) | H | $CH_3$ | OH |
| V. | 24-Hydroxymethyl-$H_2B_{1a}$ (24-OH-$H_2B_{1a}$) | A | $CH_2CH_3$ | OH |
| VI. | 24-Hydroxymethyl-$H_2B_{1b}$ (24-OH-$H_2B_{1b}$) | A | $CH_3$ | OH |
| VII. | 24-Hydroxymethyl-$H_2B_{1a}$-Monosaccharide (24-OH-$H_2B_{1a}$-MS) | H | $CH_2CH_3$ | OH |
| VIII. | 24-Hydroxymethyl-$H_2B_{1b}$-Monosaccharide | H | $CH_3$ | OH |

TABLE I-continued

| Metabolic Derivative Compounds | $R_1$ | $R_2$ | $R_3$ |
|---|---|---|---|
| (24-OH-$H_2B_{1b}$-MS) | | | |

TABLE EXAMPLE 1
ENZYMATIC SYNTHESIS USING IVERMECTIN AS SUBSTRATES

| Incubation Components | Incubation Samples | | | |
|---|---|---|---|---|
| | 1 | 2 | 3 | 4 |
| Oleic acid | 3 mg | 3 mg | 3 mg | 3 mg |
| Cholesterol | 1 mg | 1 mg | — | — |
| Na-Taurocholate | 1.0 ml | 1.0 ml | 1.0 ml | 1.0 ml |
| Enzyme (cholesterol esterase) | 0.5 ml | 1.0 ml | 1.0 ml | 1.0 ml |
| Compound III, Table I | — | — | 1 mg | — |
| Compound V, Table I | — | — | — | 800 ng 2 μg |

Incubation samples 1 and 2 were used as controls.

Incubation sample 4 consisted of two substrates; radiolabeled (tritium) substrate of 800 ng and non-radiolabeled substrate of 2 μg. Thus, sample 4 consisted of radiolabeled liver metabolite isolated from 1 kg steer liver mixed with 2.4 μg of non-radiolabeled metabolite isolated from in vitro steer liver microsome incubation. The total disintegration per minute (dpm) in the radiolabeled substrate was found to be 5201 dpm [100 μl counted; total 2 ml].

Incubation time of the incubation samples was 5 hours which was determined by monitoring the reaction by HPLC and, for sample 4, scintillation counting of the radioactive product.

The incubates of the samples were then extracted with chloroform:ethanol (2:1, v/v) and the organic phase was removed and evaporated to dryness under nitrogen.

The proportion of cholesterol (starting material) and cholesterol oleate (product) found in samples 1 and 2 were different. The sample 1 reaction was less complete, indicating that the duration of incubation time did not contribute to the completion of the reaction. The product of sample 3 did not show any product spot on tlc.

After extraction, all of sample 4 was dissolved in 100 μl CH$_3$CN/MeOH (6:4, v/v) and analyzed by HPLC under a gradient condition. The effluent was collected at 1 minute intervals and scintillation counted. The radioactivity histogram showed a new maJor peak retention time of 75–80 minutes. The fact that the product of sample 4 was eluted by HPLC in the same region as previously found for the non-polar metabolites in steer liver indicates that oleic acid is probably the acid portion of the in vivo metabolite.

EXAMPLE 2

IN VITRO SYNTHESIS OF FATTY ACID ESTERS OF 24-HYDROXYMETHYL-IVERMECTIN

Radiolabeled or unlabeled 24-OH-$H_2B_{1a}$ (compound V, Table I) or 24-OH-$H_2B_{1b}$ (compound VI, Table I) (5000 dpm, or 2–3 μg) was mixed with 3 mg of oleic acid in 0.2 ml acetone in a 50 ml flask. One ml of potassium phosphate (0.154M, pH 6.2, containing 0.01M sodium taurocholate) was added to the flask. Cholesterol esterase (10 units) in 1 ml potassium phosphate was added and the mixture was incubated at 37° C. for 2 hours.

At the end of the incubation, 2 ml of buffer was added and extracted with equal volumes of chloroform/ethanol (2:1 v/v). The layers were separated by centrifugation, the organic layer was removed and evaporated to dryness. For HPLC analysis, the sample was redissolved in methanol and chromatographed under an isocratic HPLC condition (CH$_3$CN:CH$_3$OH:H$_2$O; 59.4:39.6:1, v/v/v).

Product was recovered from the HPLC effluent at retention times of 38–40 minutes and confirmed to be the oleic acid ester of 24-OH-$H_2B_{1b}$ (compound VI, Table I) by Fast Atom Bombardment-Mass Spectrometry (FAB-MS spectra).

What is claimed is:

1. An ivermectin derivative compound having the structure:

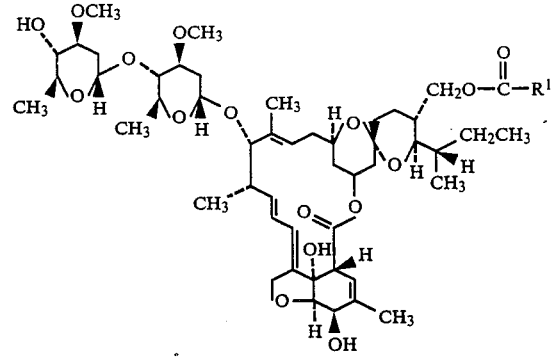

wherein $R^1$ is a straight chain or branched $C_2$–$C_{20}$ fatty acid residue.

2. The compound of claim 1 wherein $R^1$ is a straight chain or branched $C_8$–$C_{20}$ fatty acid residue.

3. The compound of claim 2 wherein said fatty acid residue is a member selected from the group consisting of $C_{13}H_{27}$, $C_{15}H_{31}$, $C_{17}H_{33}$ or $CH_3(CH_2)_4(CH=CHCH_2)_4CH_2CH_3$.

* * * * *

UNITED STATES PATENT AND TRADEMARK OFFICE
CERTIFICATE OF CORRECTION

PATENT NO. : 4,963,667

DATED : October 16, 1990

INVENTOR(S) : S.H. Lee Chiu, et al

It is certified that error appears in the above-identified patent and that said Letters Patent is hereby corrected as shown below:

On the title page in the abstract the formula should be deleted to appear as show.

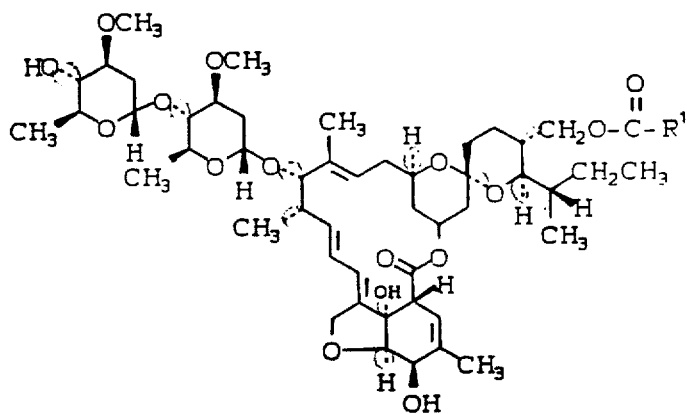

Signed and Sealed this

Twenty-third Day of June, 1992

*Attest:*

DOUGLAS B. COMER

*Attesting Officer*   *Acting Commissioner of Patents and Trademarks*